US009675975B2

(12) United States Patent
Lin et al.

(10) Patent No.: US 9,675,975 B2
(45) Date of Patent: Jun. 13, 2017

(54) GAS-BASED MICROFLUIDIC DEVICES AND OPERATING METHODS THEREOF

(71) Applicant: Shaoxing PushKang Biotechnology CO., LTD, Shaoxing, Zhejiang Province (CN)

(72) Inventors: Chia-Hui Lin, Shaoxing (CN); Bo Yu, Shaoxing (CN); Yi-Feng Yang, Shaoxing (CN)

(73) Assignee: SHAOXING PUSHKANG BIOTECHNOLOGY CO., LTD., Shaoxing, Zhejiang Province (CN)

( * ) Notice: Subject to any disclaimer, the term of this patent is extended or adjusted under 35 U.S.C. 154(b) by 197 days.

(21) Appl. No.: 14/800,696

(22) Filed: Jul. 15, 2015

(65) Prior Publication Data

US 2016/0144363 A1 May 26, 2016

(30) Foreign Application Priority Data

Nov. 20, 2014 (CN) .......................... 2014 1 0667532

(51) Int. Cl.

| | |
|---|---|
| ***B01L 3/00*** | (2006.01) |
| ***G01N 21/07*** | (2006.01) |
| *G01N 33/53* | (2006.01) |
| *B01J 19/00* | (2006.01) |

(52) U.S. Cl.

CPC ....... *B01L 3/502738* (2013.01); *B01L 3/5027* (2013.01); *B01L 3/50273* (2013.01); *B01L 3/502723* (2013.01); *B01L 3/502753* (2013.01); *B01L 2200/0605* (2013.01); *B01L 2200/0621* (2013.01); *B01L 2300/0803* (2013.01); *B01L 2400/0409* (2013.01); *B01L 2400/06* (2013.01); *B01L 2400/0688* (2013.01)

(58) Field of Classification Search

CPC ........... B01L 3/502753; B01L 3/50273; B01L 3/5027; B01L 3/502723; B01L 3/502738; B01L 2200/0605; B01L 2400/06; B01L 2300/0803; B01L 2400/0688; B01L 2400/0409; B01L 2200/0621

See application file for complete search history.

(56) References Cited

U.S. PATENT DOCUMENTS

2005/0026301 A1* 2/2005 Petithory ............ B01L 3/50273 436/180

2013/0074962 A1* 3/2013 Garcia da Fonseca .............. B01L 3/50273 137/597

* cited by examiner

*Primary Examiner* — Jennifer Wecker

(74) *Attorney, Agent, or Firm* — Cheng-Ju Chiang

(57) ABSTRACT

Gas-based microfluidic devices and operating methods of gas-based microfluidic devices are provided. The gas-based microfluidic devices comprise a drive module and a microfluidic platform, in which the microfluidic platform further comprises a microfluidic element having an injection chamber, a process chamber, an air chamber, an overflow channel, a barrier, and at least one detection chamber. Gases in the air chamber enable solutions to move toward the direction opposite to the centrifugal force applied by the drive module. Accordingly, the operating methods utilize the gases compressed in the air chamber to move solutions to difference components in the microfluidic element.

17 Claims, 13 Drawing Sheets

INJECTING A FIRST TEST SOLUTION INTO AN INJECTION CHAMBER OF A GAS-BASED MICROFLUIDIC DEVICE

↓

ROTATING THE MICROFLUIDIC PLATFORM TO TRANSFER THE FIRST TEST SOLUTION IN THE INJECTION CHAMBER TO THE PROCESS CHAMBER

↓

INCREASING THE ROTATIONAL SPEED TO A FIRST RPM TO ACTUATE THE FIRST TEST SOLUTION TO COMPRESS A FIRST GAS IN THE AIR CHAMBER

↓

DECREASING THE ROTATIONAL SPEED TO A SECOND RPM TO ALLOW THE FIRST GAS TO ACTUATE THE FIRST TEST SOLUTION TO FLOW TO THE DETECTION CHAMBER

FIG. 7

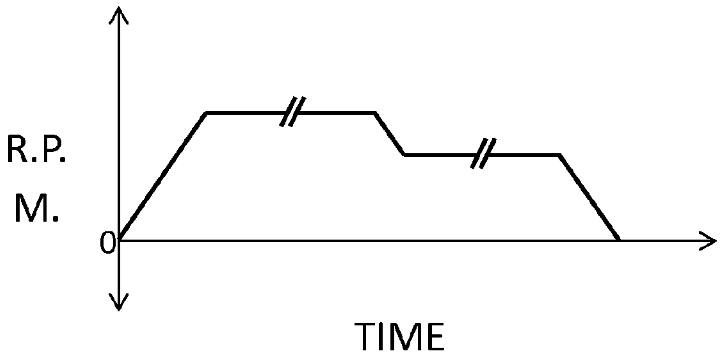

FIG. 8

GAS-BASED MICROFLUIDIC DEVICES AND OPERATING METHODS THEREOF

CROSS-REFERENCE TO RELATED APPLICATION AND CLAIM OF PRIORITY

This application claims the benefit of Chinese Patent Application No. 201410667532.0, filed on Nov. 20, 2014, in the State Intellectual Property Office of the People's Republic of China, the disclosure of which is incorporated herein in its entirety by reference.

1. Technical Field

At least one embodiment of the present invention relates to gas-based microfluidic devices and operating methods thereof. More particularly, the gas-based microfluidic devices and the operating methods are based on the utilizations of air pressure to transfer liquid.

2. Description of the Related Art

Sample preparation and solution metering are complex tasks in the art of analysis, in which both require well-trained technicians and advanced instruments to perform. Sample preparation and solution metering play a central role in obtaining qualified samples for analysis. However, costs on training technicians and purchasing instruments built a high barrier to found an analysis laboratory. Large institutes such as research centers and hospitals may be capable of affording an analysis department, but local workshops and clinics, which are standing on the first line, lack the ability to own an in-house laboratory. Those local workshops and clinics usually outsource the tasks including detection, analysis, and diagnosis to professional laboratories. Nevertheless, the extra transit time to those professional laboratories may lead to several shortcomings includes being time-consuming and increasing the possibility of sample denaturation.

Recent development in the field of lab-on-a-chip (LOC) successfully compromises the above-mentioned shortcomings. Typical advantages of a LOC are the low fluid volumes consumption, low fabrication costs, fast analysis, and high portability. The LOC technology soon becomes an important part of efforts to improve global health, particularly through the development of point-of-care testing (POCT) devices. The LOC technology promises a future allowing healthcare providers in poorly equipped clinics to perform diagnostic tests onsite. Similar to conventional technologies, sample preparation and sample volume metering are important procedures to enhance accuracy of the LOC-based devices.

Conventional LOC-based devices commercially available on the market usually provide rough, inconsistent results because many LOC-based devices lack for the ability to perform sample preparations. For example, cholesterol meters and glucometers commonly seen in life are small and portable devices which are convenient to use. However, those LOC-based devices, using crude samples without preliminary filtration as subjects, only provide rough results with low specificity. The accuracy is not qualified for medical institutes which require accurate data to determine the medical condition for a patient.

One common sample preparation is centrifugation. Centrifugation provides a fast but low-cost way to purify crude samples. Unlike filter membranes, centrifugation can be simply applied on various substances without the need of having different modules for different substances. Centrifugation utilizes the centrifugal force and the density of substances to isolate subsamples. This preliminary procedure may significantly elevate the accuracy of subsequent procedures. For example, EPA staff may use centrifugation to separate the suspended solids from a water sample and provides the supernatant for colorimetric analysis. In another example, a laboratory technician may use centrifugation to isolate the precipitated particles from a urine sample and exams the presence of crystalluria in the precipitated particles under a microscope.

Conventional LOC-based devices also show deficiency of the ability to perform accurate metering. In the field of bioanalysis, solution metering is usually applied on reagents and test materials to reduce variations and provide stable and accurate results. Typical metering methods can be classified into either manual category or automate category. The manual category, due to the possible manmade errors, hardly provides solutions in a consistent volume and usually induces variations in the subsequent procedures. For example, triglyceride levels in blood are considered to be below 200 mg/dL in a health adult. In a standard 6-μL protocol, injecting 8 μL of blood sample into the detection chamber of a LOC-based device would result in significant differences. A subject with a triglyceride level of 180 mg/dL would be diagnosed as one at high risk since the result indicates that the triglyceride level of the subject is 240 mg/dL. The automate category, on the other hand, usually uses capillary siphoning or wax plug to control the distribution of solutions. The capillary siphoning and wax plug, nevertheless, are highly unstable and hard to fabricate.

Accordingly, there is a need for a LOC-based device which is easy to manufacture and use, but provides stable results.

SUMMARY

At least one embodiment of the present invention provides a gas-based microfluidic device. The microfluidic device is easy to manufacture and use, but provides stable results. The gas-based microfluidic device comprises a drive module and a microfluidic platform. The drive module is configured to rotate the microfluidic platform when the microfluidic platform is mounted on the drive module. The microfluidic platform comprises a center of rotation and at least one microfluidic element, where each of the at least one microfluidic element comprises an injection chamber, a process chamber, an air chamber, an overflow channel, at least one detection chamber, and a barrier. More particularly, the injection chamber is disposed at a place near the center of rotation and configured to accept a solution. Relative to the injection chamber, the process chamber is disposed at a peripheral place on the microfluidic platform and is connected to the injection chamber. The process chamber is also connected to the air chamber and the overflow channel respectively, and connected with the at least one detection chamber through the overflow channel. The barrier is configured between the process chamber and the overflow channel to suppress the spilling of unprocessed solutions.

At least one embodiment of the present invention provides an operating method of gas-based microfluidic devices. A solution is preloaded into the injection chamber on the gas-based microfluidic device before the microfluidic platform is being rotating. The microfluidic platform then begins rotating to transfer, by the centrifugal force, the solution in the injection chamber to the process chamber. In the next step, the rotational speed of the microfluidic platform is increased to a first RPM to apply a force, indirectly by the solution, on a gas in the air chamber to compress the gas into a smaller volume. And the rotational speed of the microfluidic platform is then decreased to a second RPM to allow the gas to decompress and then transfer the solution to the at least one detection chamber.

At least one embodiment of the present invention shows a better efficiency on sample preparation. The drive module in a gas-based microfluidic device may be used to purify samples for reactions. The gas-based microfluidic device separates substances with different densities, based in part on the density gradient, in a short time and thus largely improves test results.

At least one embodiment of the present invention shows the ability to adjust and manage the transferred volume of a solution in multiple stages. In the manufacturing stage, for example, the size of the process chamber, the size of the air chamber, the radial position of the process chamber, and the radial positions of the air chamber are parameters to determine the transferred volume of solutions. In the operating stage, for example, the injected volume of solutions in the injection chamber, the first RPM, and the second RPM are parameters to determine the transferred volume of solutions.

At least one embodiment of the present invention provides stable and reproducible results. The gas-based microfluidic device, for example, can be used to transfer processed solutions to the at least one detection chamber simultaneously by the gases in the air chamber. The transference based on gases can reduce man-made errors and diminish variations among detection chambers. The gas-based microfluidic device therefore shows a better performance on stability and reproducibility.

At least one embodiment of the present invention provides a fast and easy method to operate microfluidic devices. In some embodiments, the gas-based microfluidic devices finish the sample preparation and sample dispensation in one acceleration/deceleration cycle. In the acceleration stage, the gas-based microfluidic device increases the rotational speed and utilizes the centrifugal force for sample preparation; in the deceleration stage, the gas-based microfluidic device decreases the rotational speed and utilizes the decompressing gases to transfer the processed samples to the at least one detection chamber evenly.

The gas-based microfluidic devices in some embodiments are easy to manufacture and use, but provide results with high stability and reproducibility. Several embodiments disclosed herein may apply to fields including chemical testing, biochemical testing, medical testing, water testing, environmental testing, food inspection, and the defense industry.

BRIEF DESCRIPTION OF THE DRAWINGS

FIG. 7 is a flowchart illustrating an operating method of gas-based microfluidic devices, according to some embodiments of the present invention.

FIG. 8 is a schematic graph illustrating the change in angular velocity over time of a drive module, according to some embodiments of the present invention.

DESCRIPTION OF THE PREFERRED EMBODIMENTS

The examples depicted in the following section are provided for the purpose of detailed explanation of the features of preferred embodiments, in order to enable one having ordinary skill in the art to understand the preferred embodiments.

At least one embodiment of the present invention relates to a gas-based microfluidic device comprising a drive module and a microfluidic platform. The drive module is configured to drive and control the microfluidic platform to rotate, while the microfluidic platform is configured for solution preparation and solution metering. The microfluidic platform is mounted on the drive module, and comprising a center of rotation and at least one microfluidic element. Each microfluidic element further comprises an injection chamber, a process chamber, an air chamber, an overflow channel, a barrier, and at least one detection chamber.

Figure 1A:
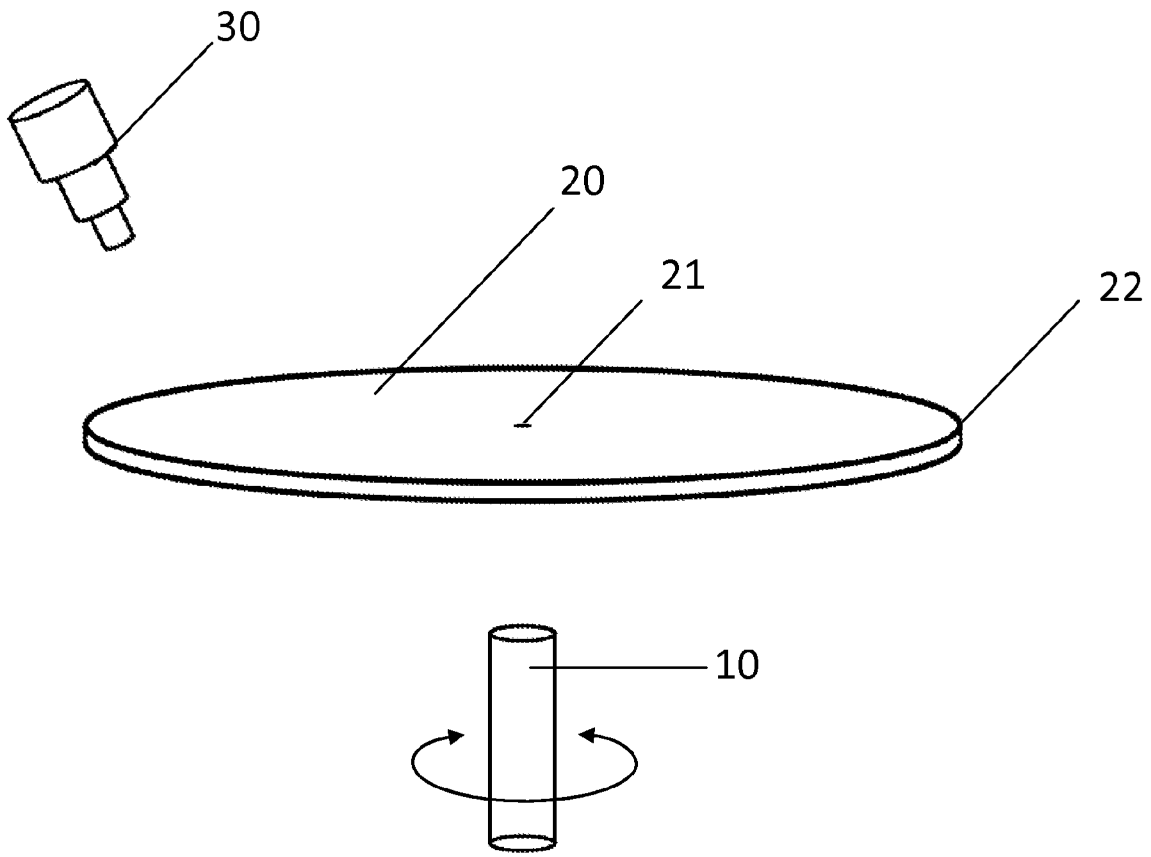
FIG. 1A is a schematic diagram illustrating a gas-based microfluidic device, according to some embodiments of the present invention.
Figure 1B:
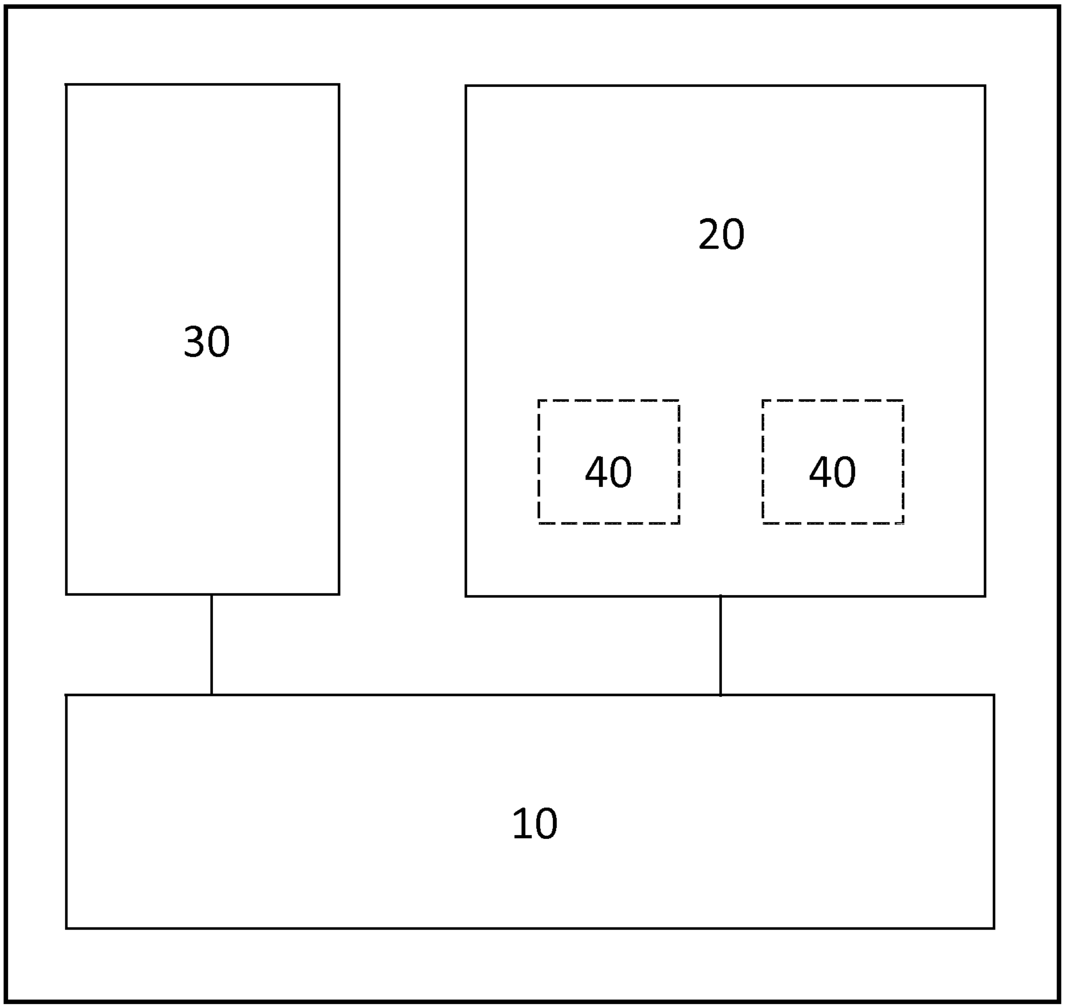
FIG. 1B is a block diagram illustrating the connections in a gas-based microfluidic device, according to some embodiments of the present invention.

FIG. 1A is a schematic diagram illustrating a gas-based microfluidic device, according to some embodiments of the present invention. The gas-based microfluidic device comprises a drive module 10 and a microfluidic platform 20. As noted previously, the drive module 10 is configured to control the rotation of the microfluidic platform 20 while the microfluidic platform 20 is configured for solution preparation and solution metering. The microfluidic platform 20 is mounted on the drive module 10 and comprising a center of rotation 21 and a circumference 22. FIG. 1B is a block diagram illustrating a gas-based microfluidic device, providing further details of the connections in the gas-based microfluidic device according to some embodiments of FIG. 1A. As illustrated in FIG. 1B, the gas-based microfluidic device comprise a drive module 10 physically connecting to a microfluidic platform 20, where at least one microfluidic element 40 is disposed on the microfluidic platform 20.

The drive module 10 illustrated in FIG. 1A may be a centrifuge. The drive module 10 would rotate the microfluidic platform 20 once the drive module 10 is activated. Note that the center of rotation 21 as used herein refers to the point the microfluidic platform 20 is rotating around during the rotation.

The microfluidic platform 20 in FIG. 1A may be formed in a circular, square, polygonal, or other radially symmetrical shapes. The material of the microfluidic platform 20 may be one selected from the group consisting of polylactide, polyethylene, polyvinyl alcohol, polypropylene, polystyrene, polycarbonate, polymethylmethacrylate, polydimethylsiloxane, polyvinylchloride, polyethylene terephthalate, polyvinylidine chloride, silicon dioxide and the combination thereof.

As illustrated in FIGS. 1A and 1B, the gas-based microfluidic device may further comprise a detection module 30 in some embodiments. The detection module 30 is electrically connected to the drive module 10 and configured to obtain or sense signals such as the test results on the microfluidic platform 20. The detection module 30 may, according to the requirements, be one selected from the group consisting of a spectrophotometer, a colorimeter, a turbidimeter, a thermometer, a pH meter, an ohmmeter, a colonometer, an image sensor, and the combinations thereof.

Figure 2:
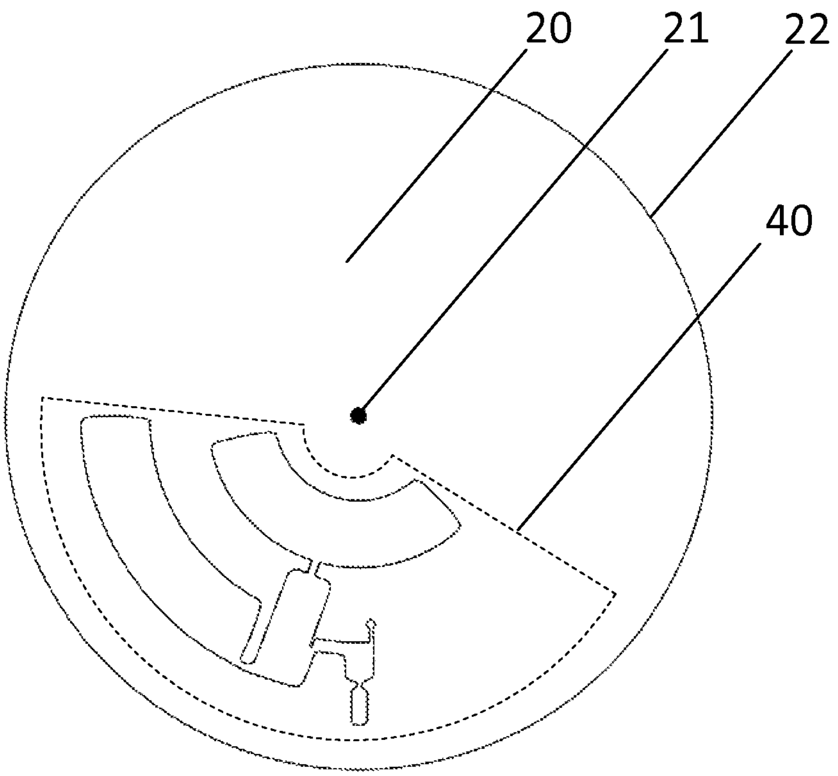
FIG. 2 is a schematic diagram illustrating a microfluidic platform, according to some embodiments of the present invention.

FIG. 2 is a schematic diagram illustrating a microfluidic platform, according to some embodiments of the present invention. The microfluidic platform 20 comprises a rotation center 21, a circumference 22, and a microfluidic element 40 configured between the center of rotation 21 and the circumference 22. In some other embodiments, the microfluidic platform 20 may comprise multiple microfluidic elements 40. The multiple microfluidic elements 40, depending on the requirements, may be fabricated as connecting or independent to each other.

Figure 3A:
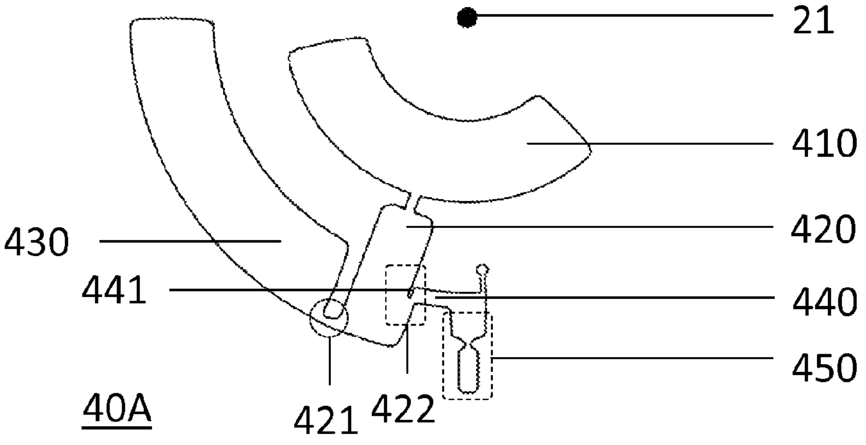
FIG. 3A is a schematic diagram illustrating a microfluidic element, according to some embodiments of the present invention.

FIG. 3A is a schematic diagram illustrating a microfluidic element, according to some embodiments of the present invention. The microfluidic structure 40A illustrated in FIG. 3A comprises an injection chamber 410, a process chamber 420, an air chamber 430, an overflow channel 440, a barrier 441, and a detection chamber 450. For the microfluidic element 40A disclosed herein, the end relatively closer to the center of rotation 21 is defined as the interior and the end relatively away from the center of rotation 21 is defined as the exterior. Accordingly, the microfluidic element 40A, from the interior to the exterior, comprises the injection chamber 410 and the process chamber 420. The air chamber 430 and the overflow channel 440 are disposed at the left side and right side to the process chamber 420 respectively, in which the process chamber 420 is connecting with the at least one detection chamber 450 through the overflow channel 440. And the barrier 441 is disposed between the process chamber 420 and the overflow channel 440. In some alternative embodiments, the air chamber 430 and the overflow channel 440, depending on the requirements, may be disposed at the same side, rather than at different sides as illustrated in FIG. 3A, to the process chamber 420.

The injection chamber 410 in FIG. 3A may be used to accommodate a first test solution, such as a solution or a sample. The solution may be a buffer solution, a wash buffer, a reagent, a solvent, or a developer. In contrast, the sample may be blood, urine, saliva, water, or liquid food. However, preferred samples are the one comprising substances with a first density and substances with a second density, in which the first density is higher than the second density. For example, a preferred sample may be the blood sample comprising blood cells and serum, the urine sample comprising urine proteins and body fluid, or the water sample comprising silt and water.

The process chamber 420 in FIG. 3A is connecting with different components and configured for sample preparation. The process chamber 420 connected with the injection chamber 410 is also connecting to the air chamber 430, through a first connection channel 421, and the overflow channel 440, through a second connection channel 422. After the drive module has been operated for a period, substances in the first test solution will be distributed, by the centrifugal force, in the microfluidic element 40A according to the density gradient. Most of the substances with high density are settling at the bottom of the process chamber 420 while most of the substances with low density are suspending at the surface side, which is closer to the second connection channel 422. In some preferred embodiments of FIG. 3A, the distance between the center of rotation 21 and the first connection channel 421 is greater than that between the center of rotation 21 and the second connection channel 422.

The air chamber 430 in FIG. 3A contains gases. After the drive module is activated, the first test solution in the injection chamber 410 flows into the process chamber 420 and seals the first connection channel 421 to form an airtight space. Subsequently, the increasing rotational speed of the drive module would apply a stronger centrifugal force on the gases in the air chamber 430 through the first test solution, and the gases in the air chamber 430 would thus be compressed by the increasing pressure. In contrary, the following step of decreasing the rotational speed of the drive module would result in the restoration of gas volume in the air chamber 430. In some preferred embodiments, the solubility of the gas in the first test solution is less than 20% percent by volume when at room temperature and pressure.

The overflow channel 440 in FIG. 3A is microfluidic channel connecting between the process chamber 420 and detection chambers 450. The overflow channel 440 allows solutions to flow between the process chamber 420 and detection chambers 450. As illustrated in FIG. 3A, a barrier 441 is configured between the process chamber 420 and the overflow channel 440 to suppress solutions from spilling into the overflow channel 440 and the detection chamber 450 before a predetermined condition. For example, if the volume of the first test solution flowing into the process chamber 420 is greater than the volume of air be expelling from the microfluidic element 40A, the flow of the first test solution would be highly unstable because of the increasing air pressure in the process chamber 420. The unstable flow of the first solutions will leak and spill into the overflow channel 440 and the detection chamber 450 unintentionally and intervene in the control of reactions and timings. Therefore, the barrier 441 between the process chamber 420 and overflow channel 440 is configured to stabilize the flow of the first test solution and suppress the possibility that the first test solution spills into the overflow channel 440 and the detection chamber 450.

The detection chamber 450 in FIG. 3A is used to contain a test material, such as a solution, a sample, or a test strip. The solution may be a buffer solution, a wash buffer, a reagent, a solvent, or a developer. In contrast, the test strip may be litmus, a chlorine dioxide test, a water hardness test strip blood, a glucose test strip, an ovulation test strip, a colloidal gold-based test strip, or a Multistix test strip. In some embodiments, the first test solution in the process chamber 420 flowed into the detection chamber 450 interacts with the test materials preloaded in the detection chamber 450 to yield test results.

FIG. 3A provide an exemplary microfluidic element in accordance with some embodiments of the present invention. In some other embodiments, however, the components of the microfluidic elements 40A may be varied in number, structure, or configuration, based on design considerations (e.g., test requirements and cost).

Figure 3B:
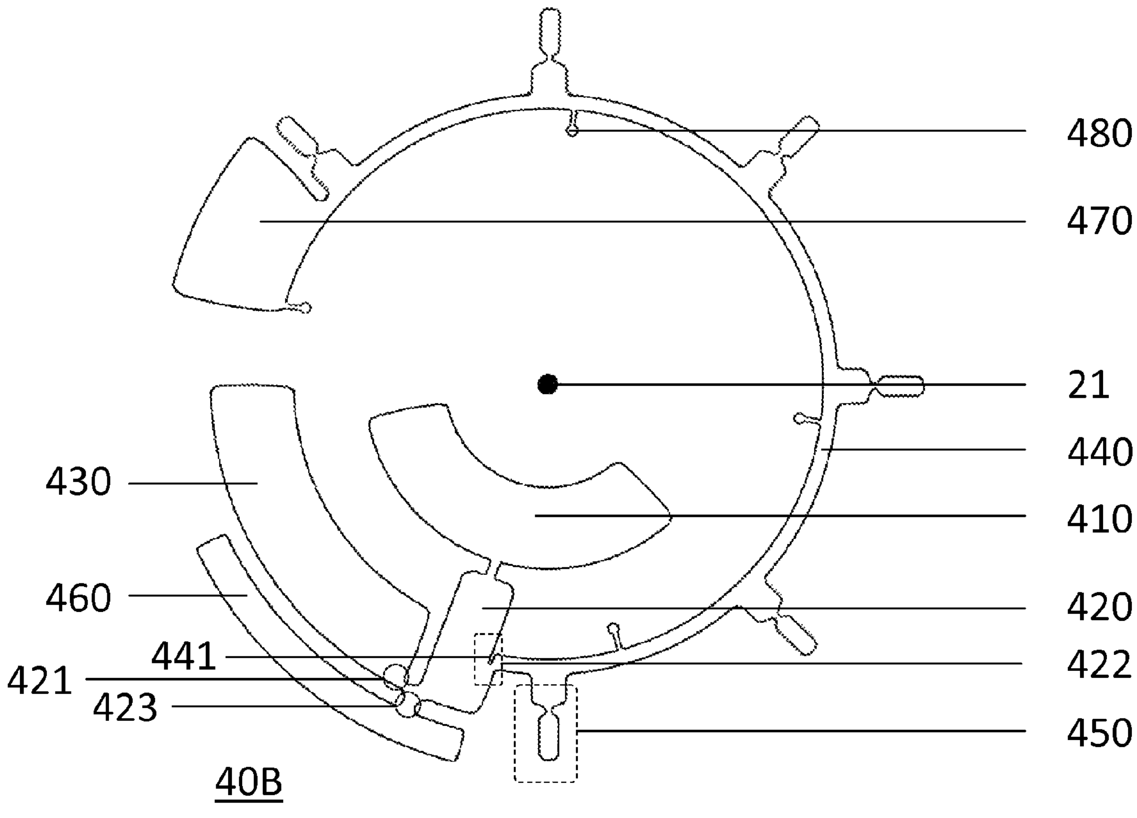
FIG. 3B is a schematic diagram illustrating a microfluidic element, according to some embodiments of the present invention.

FIG. 3B is a schematic diagram illustrating a microfluidic element, according to some embodiments of the present invention. The microfluidic element 40B in FIG. 3B comprises an injection chamber 410, a process chamber 420, an air chamber 430, an overflow channel 440, a barrier 441, six detection chambers 450, a storage chamber 460, a waste chamber 470, and four air vents 480. For the microfluidic element 40B disclosed herein, the end relatively closer to the center of rotation 21 is defined as the interior and the end relatively away from the center of rotation 21 is defined as the exterior. Accordingly, the microfluidic element 40B, from the interior to the exterior, comprises the injection chamber 410, the process chamber 420, and the storage chamber 460. The air chamber 430 and the overflow channel 440 are disposed at the left side and right side to the process chamber 420 respectively, in which the process chamber 420 is further connecting with the six detection chambers 450 and the waste chamber 470 through the overflow channel 440. The barrier 441 is disposed between the process chamber 420 and the overflow channel 440. In some alternative embodiments, the air chamber 430 and the overflow channel 440, depending on design considerations, may be disposed at the same side, rather than at different sides as illustrated in FIG. 3B, to the process chamber 420.

The process chamber 420 in FIG. 3B is connecting with different components and configured for sample preparation. The process chamber 420 connected with the injection chamber 410 is also connecting to the air chamber 430, the overflow channel 440, and the storage chamber 460 through a first connection channel 421, a second connection channel 422, and a third connection channel 423 respectively. The configurations and connections between the process chamber 420 and other components of the microfluidic element 40B may be varied in other embodiments. In some preferred embodiments, the distance between the center of rotation 21 and the second connection channel 422 is smaller than or equal to that between the center of rotation 21 and the third connection channel 423. In some other preferred embodiments, the third connection channel 423 is connected to the bottom of the process chamber 420. In still some other preferred embodiments, the process chamber 420 and the storage chamber 460 are connected by a capillary channel.

The storage chamber 460 in FIG. 3B may be used to accommodate the high density substances precipitated from the first test solution after the operation of the drive module. The multi-chamber design of the microfluidic element 40B compartmentalizes substances with different densities from the first test solution and stores the substances into the process chamber 420, the storage chamber 460, and other chambers to improve the purification efficiency of the microfluidic element 50B. For example, if the drive module increases the rotational speed, low density substances will suspend in the process chamber 420 and high density substances will precipitate in the storage chamber 460 by the centrifugal force. In contrast, if the drive module decreases the rotational speed in the subsequent steps, the low density substances once surged into the air chamber will be pushed back to the process chamber 420, while those high density substances compartmentalized in the storage chamber 460 will be less affected by the current flowing in the exterior side of the microfluidic element 50B.

The overflow channel 440 in FIG. 3B is surrounding the center of rotation 21. The two ends of the overflow channel 440 are connecting with the process chamber 420 and the waste chamber 470 respectively. Furthermore, the six detection chambers 450 are disposed between the process chamber 420 and the waste chamber 470, in which the six detection chambers 450 are connecting to the overflow channel 440 individually.

The air vents 480 in FIG. 3B are used to release excess gases, in order to balance the internal air pressure of the microfluidic element 40B. More particularly, the air vents 480 may be used to reduce the resistance from the internal air pressure against the movements of the first test solution in the microfluidic element 40B. The air vents 480 may also be used to expel bubbles occasionally contained in the first test solution when the first test solution is moving in the microfluidic element 40B. In some preferred embodiments, air vents 480 are also configured on several other components (e.g., the injection chamber 410, the process chamber 420, or the waste chamber 470) of the microfluidic element 40B based on design considerations.

The waste chamber 470 in FIG. 3B is configured to accept excess fluid such as the first test solution. If the drive module decreases the rotational speed, the first test solution in the process chamber 420 will flow into the overflow channel 440 and be dispensed to the detection chambers 450. The first solution exceeded the capacity of the detection chambers will flow along the overflow channel 440 and enter the waste chamber 470.

FIG. 3B provide an exemplary microfluidic element in accordance with some embodiments of the present invention. In some other embodiments, however, the components of the microfluidic elements 40B may be varied in number, structure, or configuration, based on design considerations (e.g., test requirements and cost).

Figure 3C:
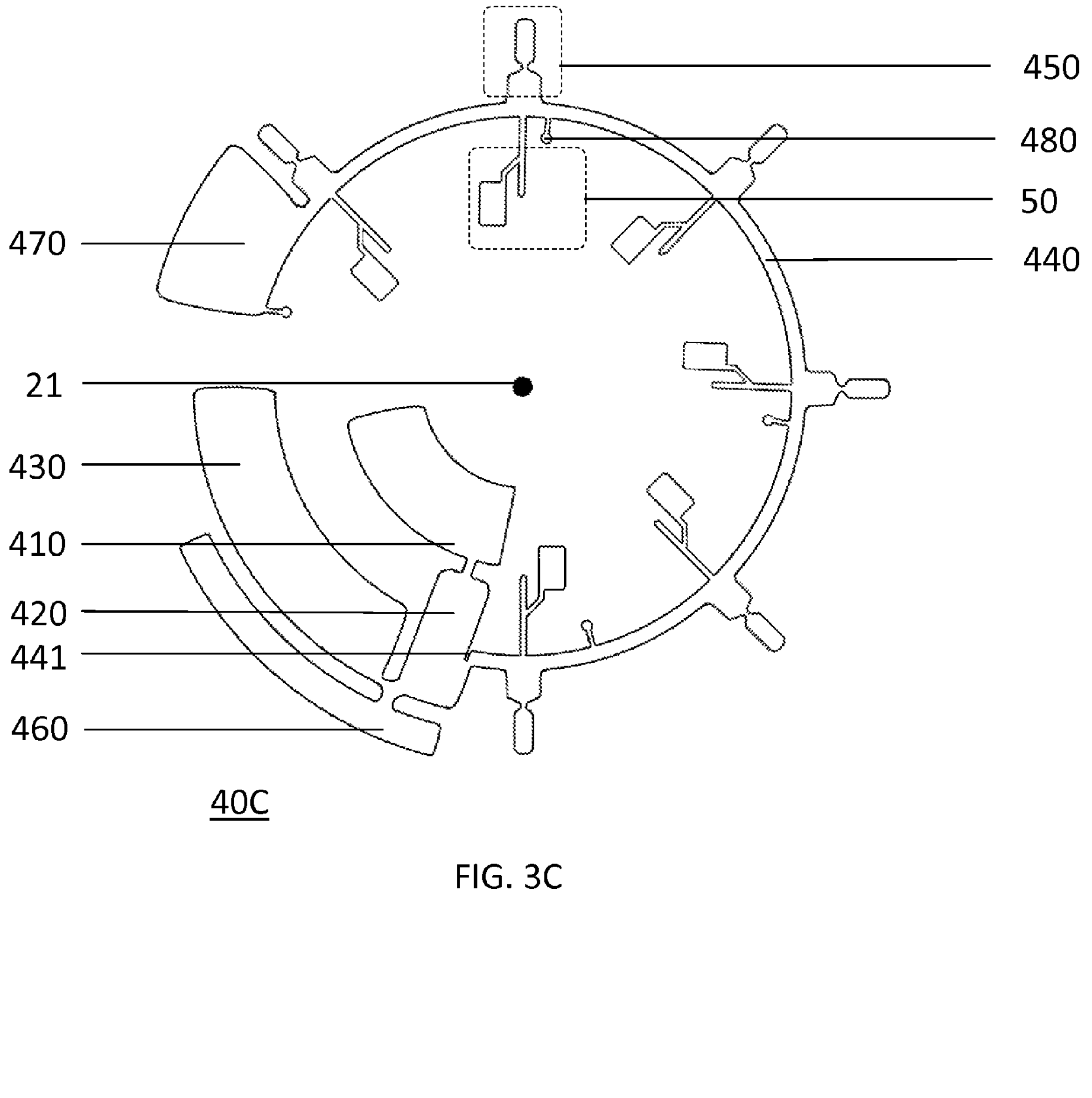
FIG. 3C is a schematic diagram illustrating a microfluidic element, according to some embodiments of the present invention.

FIG. 3C is a schematic diagram illustrating a microfluidic element, according to some embodiments of the present invention. The microfluidic element 40C in FIG. 3C comprises an injection chamber 410, a process chamber 420, an air chamber 430, an overflow channel 440, a barrier 441, six detection chambers 450, six subsidiary microfluidic elements 50, a storage chamber 460, a waste chamber 470, and four air vents 480. For the microfluidic element 40C, the end relatively closer to the center of rotation 21 is defined as the interior and the end relatively away from the center of rotation 21 is defined as the exterior. Accordingly, the microfluidic element 40B, from the interior to the exterior, comprises the injection chamber 410, the process chamber 420, and the storage chamber 460. The air chamber 430 and the overflow channel 440 are disposed at the left side and right side to the process chamber 420 respectively, while the storage chamber 460 is disposed at the exterior side to the process chamber 420. The two ends of the overflow channel 440 are connecting with the process chamber 420 and the waste chamber 470 respectively. Furthermore, the six detection chambers 450 and the six subsidiary microfluidic elements 50 are configured between the process chamber 420 and the waste chamber 470, in which the six detection chambers 450 and the six subsidiary microfluidic elements 50 are connecting to the overflow channel 440.

The subsidiary microfluidic chambers 50 in FIG. 3C are configured to accommodate a second test solution, such as a solution or a sample. The solution may be a buffer solution, a wash buffer, a reagent, a solvent, or a developer. In contrast, the sample may be blood, urine, saliva, liquid water, or liquid food. In some preferred embodiments, the number and location of the subsidiary microfluidic elements are in correspondence with the detection chambers. As illustrated in FIG. 3C, the subsidiary microfluidic elements 50 and the detection chambers 450 are paired together and disposed at the interior side and the exterior side to the overflow channel 440 respectively. Accordingly, once the drive module is activated, the second test solution in one subsidiary microfluidic element 50 will be actuated and moved into the paired detection chamber 450. However, in some other embodiments, the number and location of the subsidiary microfluidic elements are less relevant to the detection chambers. For example, a subsidiary microfluidic element may be dispose between the process chamber and the at least one detection chamber, in which the subsidiary microfluidic element is configured to provide the second test solution to the overflow channel. In this case, the overflow channel will also be used to dispense the second test solution into the downstream detection chambers.

FIG. 3C provide an exemplary microfluidic element in accordance with some embodiments of the present invention. In some other embodiments, however, the components of the microfluidic elements 40C may be varied in number, structure, or configuration, based on design considerations (e.g., test requirements and cost).

Figure 4A:
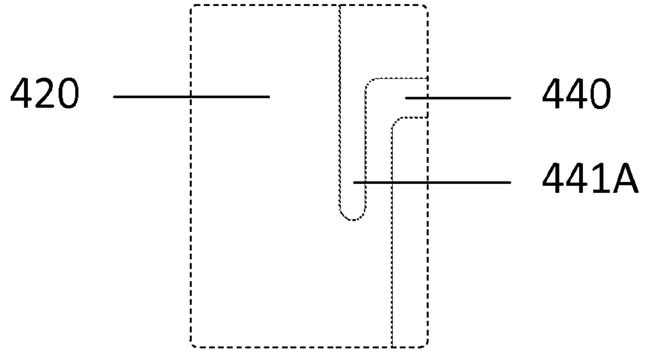
FIG. 4A is a schematic diagram illustrating a barrier, according to some embodiments of the present invention.

FIG. 4A is a schematic diagram illustrating a cover-type barrier, according to some embodiments of the present invention. The cover-type barrier 441A is a barrier configured between the process chamber 420 and the overflow channel 440, in which the barrier is protruding toward the exterior side to partially cover the overflow channel 440. When the first test solution in the injection chamber is flowing into the process chamber 420, some of the first test solution may spill to the overflow channel 440 connecting with the process chamber 420. More particularly, when the volume of the first test solution entering the process chamber 420 is greater than that of the gas expelled from the microfluidic element, the first test solution is inclined to spill into the overflow channel 440 due to the high resistance from the elevating air pressure in the process chamber 420. The leakage of the first test solution may lead to premature test results. Accordingly, the cover-type barrier 441A configured between the process chamber 420 and the overflow channel 440 is used to suppress the spillage of the first test solution to the overflow channel 440 while not largely change the direction of the flow.

Figure 4B:
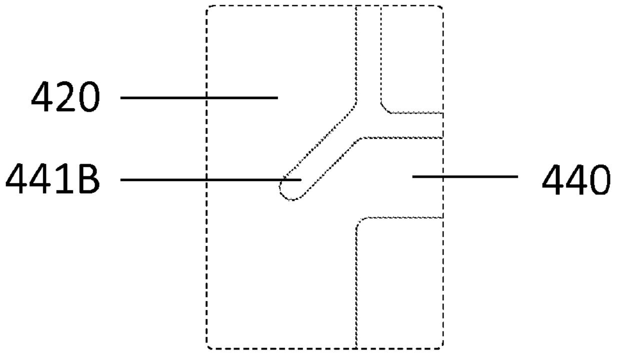
FIG. 4B is a schematic diagram illustrating a barrier, according to some embodiments of the present invention.

FIG. 4B is a schematic diagram illustrating a slope-type barrier, according to some embodiments of the present invention. The slope-type barrier 441B is a barrier configured between the process chamber 420 and the overflow channel 440, in which the barrier is protruding toward the exterior and inner side of the process chamber 420 to partially cover the overflow channel 440. When the first test solution in the injection chamber is flowing into the process chamber 420, some of the first test solution may spill to the overflow channel 440 connecting with the process chamber 420. Accordingly, the slope-type barrier 441B configured between the process chamber 420 and the overflow channel 440 is used to channel the first test solution. For example, when the first test solution in the injection chamber is flowing in, the barrier would channel the first test solution away from the overflow channel 440 to decrease the spillage of the first test solution to the overflow channel 440. In contrast, when the first test solution is moving from the air chamber 430 back to the process chamber 420 in the subsequent steps that the drive module is decreasing the rotational speed, the slope-type barrier 441B would channel the elevating fluid to the overflow channel 440.

Figure 4C:
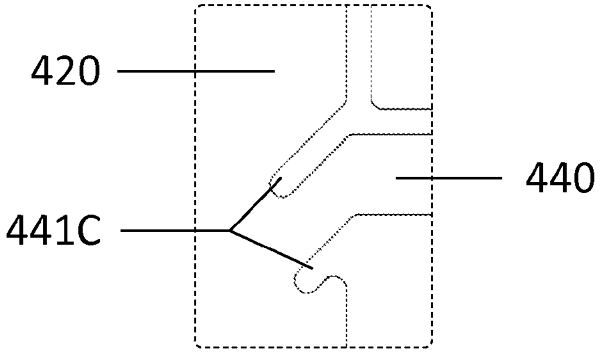
FIG. 4C is a schematic diagram illustrating a barrier, according to some embodiments of the present invention.

FIG. 4C is a schematic diagram illustrating a twin-type barrier, according to some embodiments of the present invention. The twin-type barrier 441C comprises two barriers configured between the process chamber 420 and the overflow channel 440, in which the two barriers are both protruding toward the inner side of the process chamber 420 to partially cover the overflow channel 440. When the first test solution in the injection chamber is flowing into the process chamber 420, some of the first test solution may spill into the overflow channel 440 connecting with the process chamber 420. More particularly, when the flow velocity of the first test solution from the injection chamber to the process chamber 420 is higher than a threshold, the first test solution would bounce off from the walls or the liquid surface and spill into the overflow channel 440. Accordingly, the slope-type barrier 441C is configured to diminish the spillage. The barrier closer to the interior of the microfluidic platform is configured to channel the first test solution away from the overflow channel 440 and thus reduce the premature influx of first test solution. The barrier closer to the exterior of the microfluidic platform is configured to block the first test solution bouncing into the overflow channel 440. In some alternative embodiments, the two barriers of the twin-type barrier 441C may, depending on design considerations, have different lengths. For example, the barrier closer to the interior of the microfluidic platform may be longer than the barrier closer to the exterior of the microfluidic.

Figure 5A:
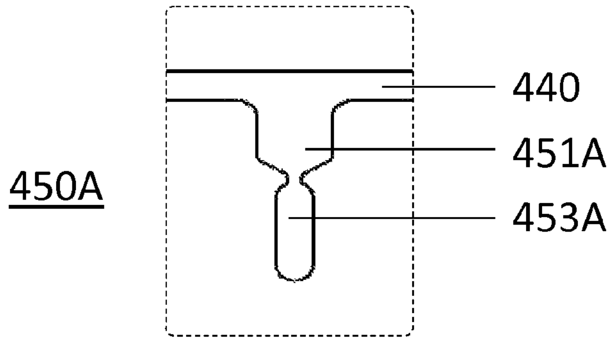
FIG. 5A is a schematic diagram illustrating a detection chamber, according to some embodiments of the present invention.

FIG. 5A is a schematic diagram illustrating a detection chamber, according to some embodiments of the present invention. The detection chamber 450A is connected to the overflow channel 440. The detection chamber 450A comprises a metering chamber 451A and a reaction chamber 453A. In the embodiments, the metering chamber 451A is connected to the overflow channel 440 while the reaction chamber 453A is connected to the metering chamber 451A. Accordingly, solutions moving from the process chamber to the overflow channel 440 would flow along the overflow channel 440 and enter the metering chamber 451A and the reaction chamber 453A.

In some embodiments of FIG. 5A, the reaction chamber 453A and the metering chamber 451A are connected by a microfluidic channel and formed in a configuration similar to a sandglass. The reaction chamber 453A herein is preferred to be configured without any air vent. In the embodiments, when solutions moving from the process chamber to the overflow channel 440, the solutions would flow along the overflow channel 440 and enter the metering chamber 451A. However, the solutions would be retained in the metering chamber 451A by external forces. The external forces include the surface tension generated by the solutions at the microfluidic channel and the air pressure in the reaction chamber 453A. Accordingly, the solutions in the metering chamber 451A would flow into the reaction chamber when the centrifugal force applied by the drive module is greater than the resistance from the surface tension and the air pressure in the reaction chamber 453A.

Figure 5B:
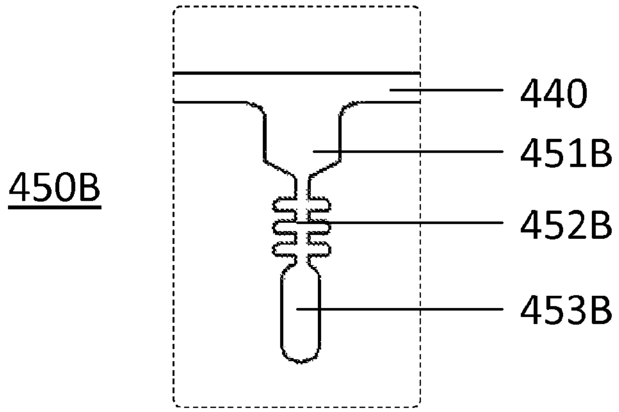
FIG. 5B is a schematic diagram illustrating a detection chamber, according to some embodiments of the present invention.

FIG. 5B is a schematic diagram illustrating a detection chamber, according to some embodiments of the present invention. The detection chamber 450B is connected to the overflow channel 440. The detection chamber 450B further comprises a metering chamber 451B, a microvalve 452B, and a reaction chamber 453B. In the embodiments, the metering chamber 451B is connected to the overflow channel 440 while the reaction chamber 453B is connected to the metering chamber 451A through the microvalve 452B. When solutions moving from the process chamber to the overflow channel 440, the solutions would flow along the overflow channel 440 and enter the metering chamber 451B. However, the solutions would be retained in the metering chamber 451B by external forces rather than flow directly into the reaction chamber 453B. The external forces include the surface tension generated by the solutions at the microvalve. Note that the microvalve 452B further comprises two capillary arrays. Each capillary array is disposed at a side of the microvalve 452B and creates multiple liquid-air interfaces to enhance the surface tension from the solutions at the microvalve 452B. The solutions thus may be trapped by the microvalve 452B. Accordingly, the solutions in the metering chamber 451B would pass the microvalve 452B and flow into the reaction chamber 453B when the centrifugal force applied by the drive module is greater than the resistance from the surface tension. The RPM when the solution breaks the microvalve 452B is the burst frequency associated with the microvalve 452B.

Figure 5C:
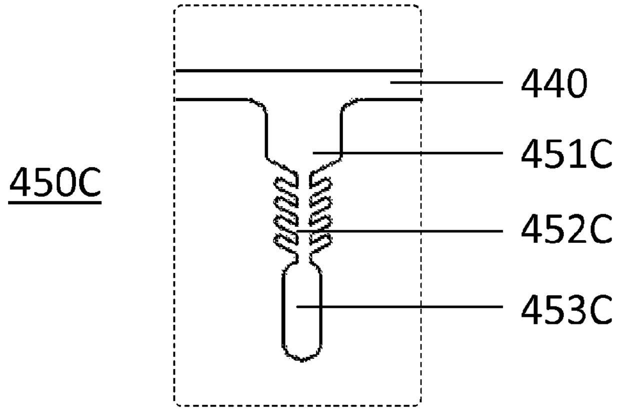
FIG. 5C is a schematic diagram illustrating a detection chamber, according to some embodiments of the present invention.

FIG. 5C is a schematic diagram illustrating a detection chamber, according to some embodiments of the present invention. The detection chamber 450C is connected to the overflow channel 440. The detection chamber 450C herein comprises a metering chamber 451C, a microvalve 452C, and a reaction chamber 453C. In the embodiments, the metering chamber 451C is connected to the overflow channel 440 while the reaction chamber 453C is connected to the metering chamber 451C through the microvalve 452C. Note that the microvalve 452C comprises two capillary arrays disposed at opposite sides of the microvalve 452B. More particularly, each capillary in the two capillary arrays has a closed end and an open end, in which the closed end is relatively close to the center of rotation 21 when compared with the open end. Accordingly, the configuration of the microvalve 452C is to suppress the solutions from flowing into the capillary arrays when the solutions are passing from the metering chamber 451C to the reaction chamber 453C.

Figure 6A:
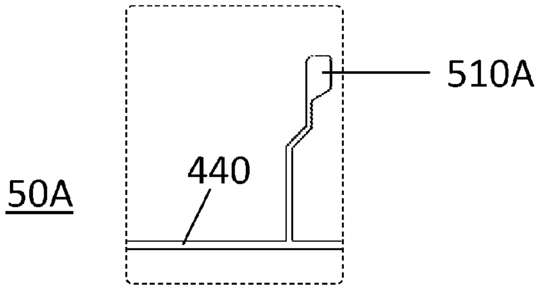
FIG. 6A is a schematic diagram illustrating a subsidiary microfluidic element, according to some embodiments of the present invention.

FIG. 6A is a schematic diagram illustrating a subsidiary microfluidic element, according to some embodiments of the present invention. The subsidiary microfluidic element 50A is connected to the overflow channel 440 and, compared to the overflow channel 440, disposed at the interior side of the microfluidic platform. The subsidiary microfluidic element 50A in FIG. 6A comprises a subsidiary injection chamber 510A used to accept a second test solution, such as a solution or a sample. The operation of the drive module would apply a centrifugal force on the second test solution in the subsidiary injection chamber 510A and actuate the second test solution to flow into the overflow channel 440.

Figure 6B:
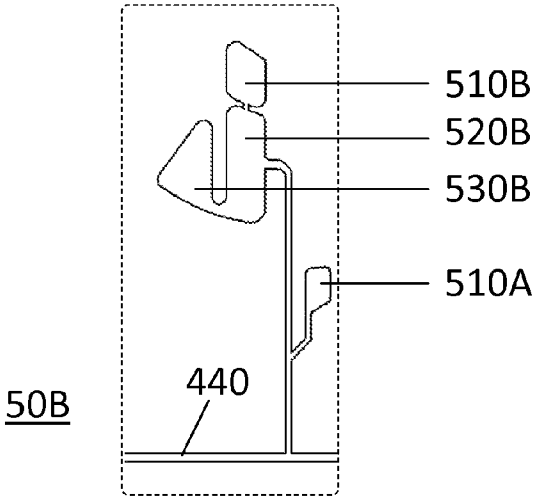
FIG. 6B is a schematic diagram illustrating a subsidiary microfluidic element, according to some embodiments of the present invention.

FIG. 6B is a schematic diagram illustrating a subsidiary microfluidic element, according to some embodiments of the present invention. The subsidiary microfluidic element 50B in FIG. 6B comprises subsidiary injection chambers 510A, 510B, a subsidiary process chamber 520B, and a subsidiary air chamber 530B. The subsidiary injection chambers 510A, 510B are configured to accept a second test solution and a third test solution respectively. During that the drive module is increasing the rotational speed, the second test solution in the subsidiary injection chamber 510A would be actuated by the elevating centrifugal force and flow into the overflow channel 440. Similarly, the third test solution in the subsidiary injection chamber 510B would be actuated by the elevating centrifugal force and flow into the subsidiary process chamber 520B and the subsidiary air chamber 530B. However, if the drive module is then decreasing the rotational speed, the third test solution would be actuated by the gases in the subsidiary air chamber 530B to flow into the overflow channel 440. Accordingly, the subsidiary microfluidic element 50B in FIG. 6B provides a mechanism to individually deliver the second test solution and the third test solution in different steps. In some other embodiments, the configurations of the subsidiary microfluidic element, the volume of solutions, and the rotational speed may be altered to manipulate the delivery timings and sequence of the second test solution and the third test solution.

Figure 6C:
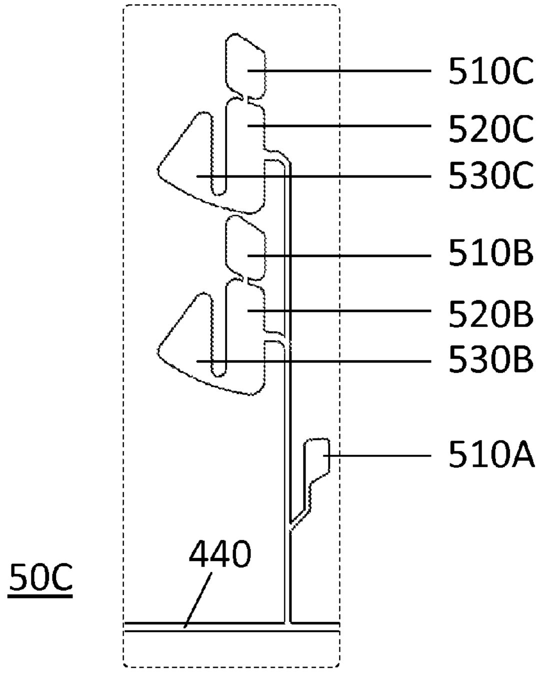
FIG. 6C is a schematic diagram illustrating a subsidiary microfluidic element, according to some embodiments of the present invention.

FIG. 6C is a schematic diagram illustrating a subsidiary microfluidic element, according to some embodiments of the present invention. The subsidiary microfluidic element 50C in FIG. 6C comprises subsidiary injection chambers 510A, 510B, 510C, subsidiary process chambers 520B, 520C, and subsidiary air chambers 530B, 530C. The subsidiary injection chambers 510A, 510B, 510C are configured to accommodate a second test solution, a third test solution, and a fourth test solution respectively. During that the drive module is increasing the rotational speed, the second test solution in the subsidiary injection chamber 510A would be actuated by the elevating centrifugal force and flow into the overflow channel 440. Similarly, the third test solution and the forth test solution in the subsidiary injection chambers 510B, 510C would be actuated by the elevating centrifugal force and flow into the subsidiary process chambers 520B, 520C and the subsidiary air chambers 530B, 530C. However, when the drive module decreases the rotational speed, the third test solution and the fourth test solution would be actuated by the gas in the subsidiary air chambers 530B, 530C to flow into the overflow channel 440 sequentially. In some other embodiments, the configuration of the subsidiary microfluidic element, the distance between the center of rotation and the subsidiary microfluidic element, the volume of solutions, and the rotational speed may be altered to manipulate the delivery timings and sequence of the second test solution, the third test solution, and the fourth test solution. Accordingly, the subsidiary microfluidic element 50C in FIG. 6C provides a mechanism to respectively deliver the second test solution, the third test solution, and the fourth test solution in different steps.

Figure 6D:
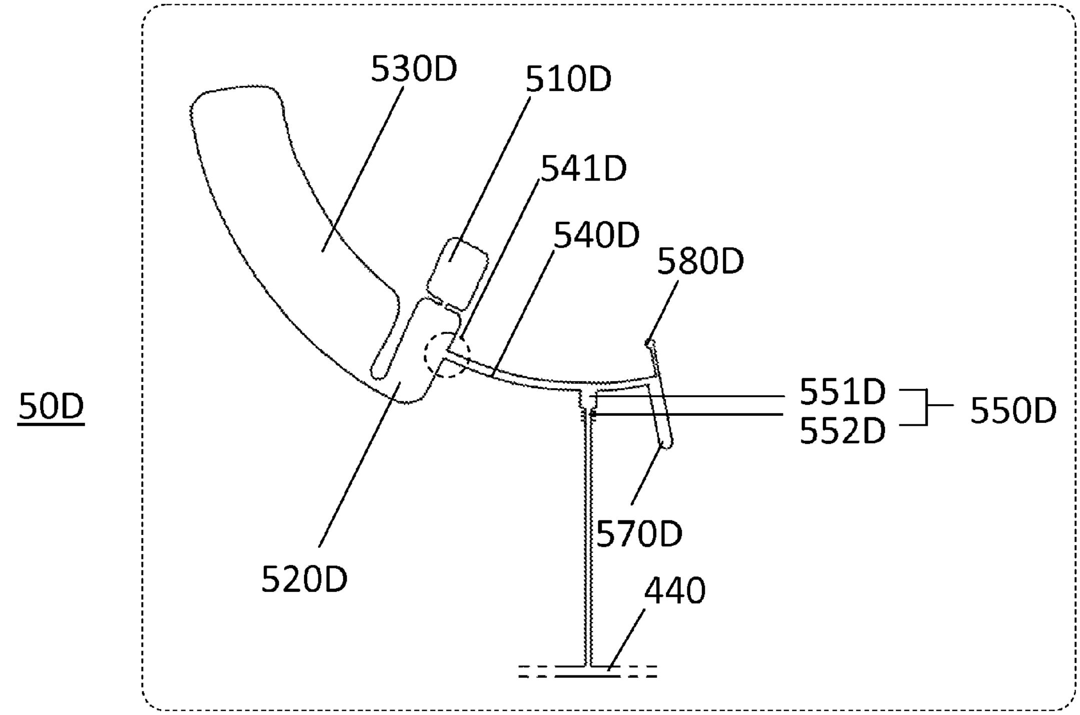
FIG. 6D is a schematic diagram illustrating a subsidiary microfluidic element, according to some embodiments of the present invention.

FIG. 6D is a schematic diagram illustrating a subsidiary microfluidic element, according to some embodiments of the present invention. The subsidiary microfluidic element 50D in FIG. 6D comprises a subsidiary injection chamber 510D, a subsidiary process chamber 520D, and a subsidiary air chamber 530D, a subsidiary overflow channel 540D, a subsidiary barrier, 541D, a subsidiary intermediate chamber 550D, a subsidiary waste chamber 570D, and a subsidiary air vent 580D. More particularly, the subsidiary intermediate chamber 550D comprises a subsidiary metering chamber 511D and a subsidiary microvalve 552D, in which the subsidiary intermediate chamber 550D is connected to and disposed between the subsidiary overflow channel 540D and the overflow channel 440. The subsidiary injection chamber 510D in FIG. 6D is configured to accommodate a second test solution, such as a solution or a sample. When the drive module increases the rotational speed, the second test solution in the subsidiary injection chambers 510D would be actuated by the elevating centrifugal force and flow into the subsidiary process chambers 520D and the subsidiary air chambers 530D. And when the drive module is then decreases the rotational speed, the second test solution would then be actuated by the gases in the subsidiary air chamber 530D to flow into the subsidiary overflow channel 540D. The second test solution would then fill the subsidiary metering chamber 551D, but the second test solution beyond the capacity of the subsidiary metering chamber 551D would flow further into the subsidiary waste chamber 570D. In contrast, the second test solution remained in the subsidiary metering chamber 551D would pass the subsidiary microvalve 552D and flow into the overflow channel 440 when the rotational speed of the drive module reaches the burst frequency associated with the subsidiary microvalve 552D.

Figure 6E:
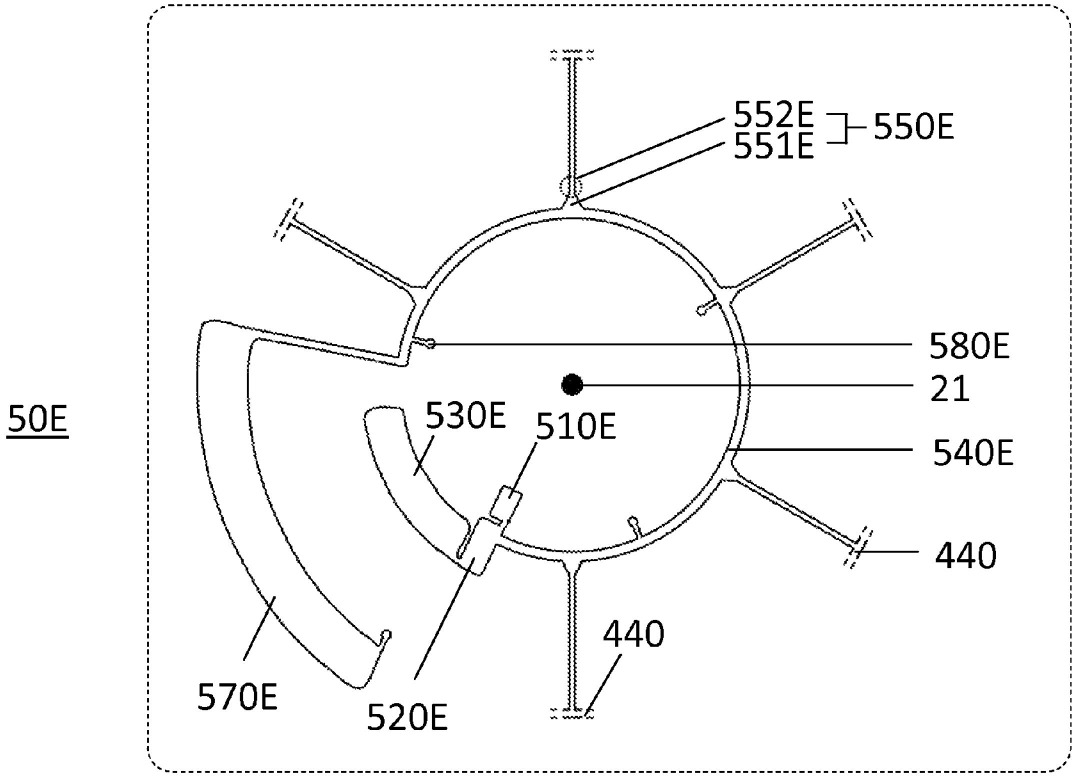
FIG. 6E is a schematic diagram illustrating a subsidiary microfluidic element, according to some embodiments of the present invention.

FIG. 6E is a schematic diagram illustrating a subsidiary microfluidic element, according to some embodiments of the present invention. The subsidiary microfluidic element 50E in FIG. 6E comprises a subsidiary injection chambers 510E, a subsidiary process chamber 520E, and a subsidiary air chamber 530E, a subsidiary overflow channel 540E, five subsidiary intermediate chambers 550E, a subsidiary waste chamber 570E, and a subsidiary air vent 580E. More particularly, the subsidiary overflow channel 540E is surrounding the center of rotation 21. The two ends of the subsidiary overflow channel 540E are connecting with the subsidiary process chamber 520E and the subsidiary waste chamber 570E respectively. Furthermore, the five subsidiary intermediate chambers 550E are disposed between the subsidiary process chamber 520E and the subsidiary waste chamber 570E, in which the five subsidiary intermediate chambers 550E are connecting to the subsidiary overflow channel 540E individually. Moreover, each subsidiary intermediate chamber 550E herein comprises a subsidiary metering chamber 551E and a subsidiary microvalve 552E.

The subsidiary injection chamber 510E in FIG. 6E is used to accommodate a second test solution, such as a solution or a sample. When the drive module increases the rotational speed, the second test solution in the subsidiary injection chambers 510E would be actuated by the elevating centrifugal force and flow into the subsidiary process chambers 520E and the subsidiary air chambers 530E. And when the drive module then decreases the rotational speed, the second test solution would then be actuated by the gas in the subsidiary air chamber 530E to flow into the subsidiary overflow channel 540E. Some of the second test solution then would fill the five subsidiary metering chambers 551E, but the second test solution beyond the capacity of the five subsidiary metering chambers 551E would flow further into the subsidiary waste chamber 570E. In contrast, the second test solution remained in the five subsidiary metering chambers 551E would pass the subsidiary microvalve 552E and flow into the overflow channel 440 respectively when the rotational speed of the drive module reaches the burst frequency associated with the subsidiary microvalve 552E.

FIGS. 6A-6E provide some subsidiary microfluidic element in accordance with some embodiments of the present invention. In some other embodiments, however, the components of the subsidiary microfluidic elements may be varied based on design considerations (e.g., test requirements and cost). For example, the components of the subsidiary microfluidic elements may be substituted by the corresponding components used in microfluidic elements. The components of the subsidiary microfluidic elements may also be varied in structure or configuration. Some features of one subsidiary microfluidic element disclosed heretofore may also be combined onto another subsidiary microfluidic element.

FIG. 7 is a flowchart illustrating an operating method of gas-based microfluidic devices, according to some embodiments of the present invention. The operating method begins with injecting a first test solution into an injection chamber of a gas-based microfluidic device. After the step of injection, the microfluidic platform starts rotating to drive the first test solution in the injection chamber to flow into a process chamber. Subsequently, the rotational speed of the microfluidic platform is increased to a first RPM. Under the first RPM, the centrifugal force generated by rotation is stronger than the air pressure of gases in the air chamber. The first test solution thus would compresses the gases in the air chamber until that the centrifugal force and the air pressure have reached balance. The rotational speed of the microfluidic platform is then decreased to a second RPM. Under the second RPM, the centrifugal force generated by rotation is weaker than the air pressure of compressed gases in the air chamber. The compressed gases therefore would decompress and actuate the first test solution to move to a detection chamber.

In some embodiments, the operating method in FIG. 7 is applied to the gas-based microfluidic device illustrated in FIG. 1B comprising the microfluidic elements 40A illustrated in FIG. 3A. The operation begins with injecting a first test solution into the injection chamber 410 of the gas-based microfluidic device. After injection, the microfluidic platform 20 begins rotating to actuate the first test solution in the injection chamber 410 to flow into the process chamber 420. Subsequently, the rotational speed of the microfluidic platform 20 is increased to a first RPM to actuate the first test solution to compress the gases in the air chamber 430. The rotational speed of the microfluidic platform 20 is then decreased to a second RPM. Under the second RPM, the centrifugal force generated by rotation is weaker than the air pressure of compressed gases in the air chamber 430. The compressed gases therefore would decompress and actuate the first test solution to move to the detection chamber 450. In some other embodiments, some test materials required for a test have been preloaded in the detection chamber 450. Under the condition, the operating method further comprises a step of obtaining, manually or automatically by a detection module 30, test results after the first test solution and the test materials is reacted.

In some embodiments, the operating method further comprises a step of determining. The step of determining is to determine the first RPM and the second RPM. During the step of decreasing the rotational speed to the second RPM, a predetermined volume of the first test solution is transferred to the overflow channel, in which the predetermined volume is positively correlating with the difference between the first RPM and the second RPM. Accordingly, manipulation of the first RPM and the second RPM provides a way to alter the predetermined volume.

FIG. 8 is a schematic graph illustrating the change in angular velocity over time of a drive module, according to some embodiments of the present invention. As in FIG. 7, the drive module in resting state is first activated to drive and rotated the microfluidic platform to generate a centrifugal force. Subsequently, the rotational speed of the drive module reaches and stays at a first RPM for a period of time. The rotational speed of the drive module is then decreased to and stays at a second RPM for a period of time. After that the test is finished, the rotational speed of the drive module would be further reduced to terminate the testing process.

FIG. 9A-9E is schematic diagrams illustrating the operation of a gas-based microfluidic device, according to some embodiments of the present invention. The microfluidic element 40 used in FIGS. 9A-9E is configured on the gas-based microfluidic element illustrated in FIG. 1B. The microfluidic element 40 in FIG. 9A comprises an injection chamber 410, a process chamber 420, an air chamber 430, an overflow channel 440, a detection chamber 450, and a storage chamber 460.

Figure 9A:
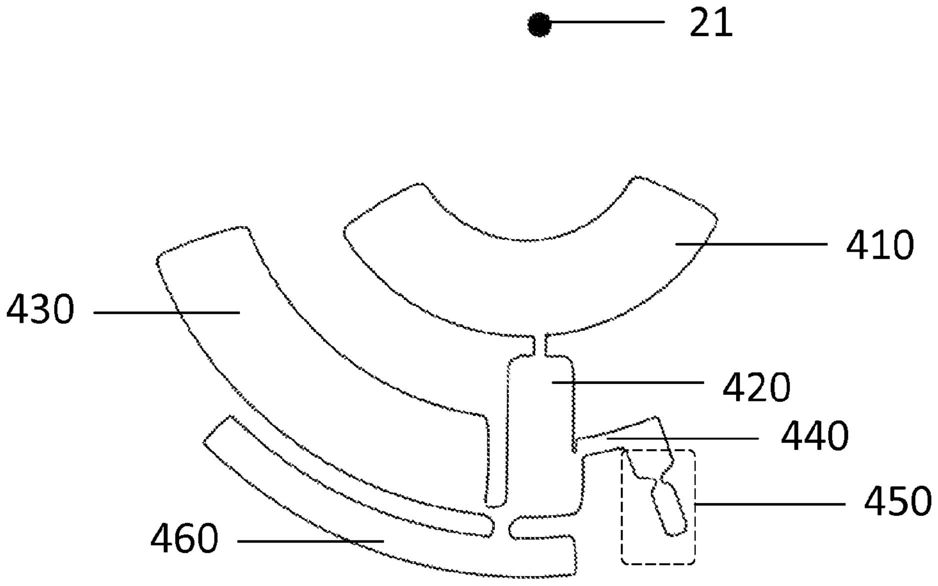
FIG. 9A-9E is schematic diagrams illustrating the operation of a gas-based microfluidic device, according to some embodiments of the present invention.
Figure 9B:
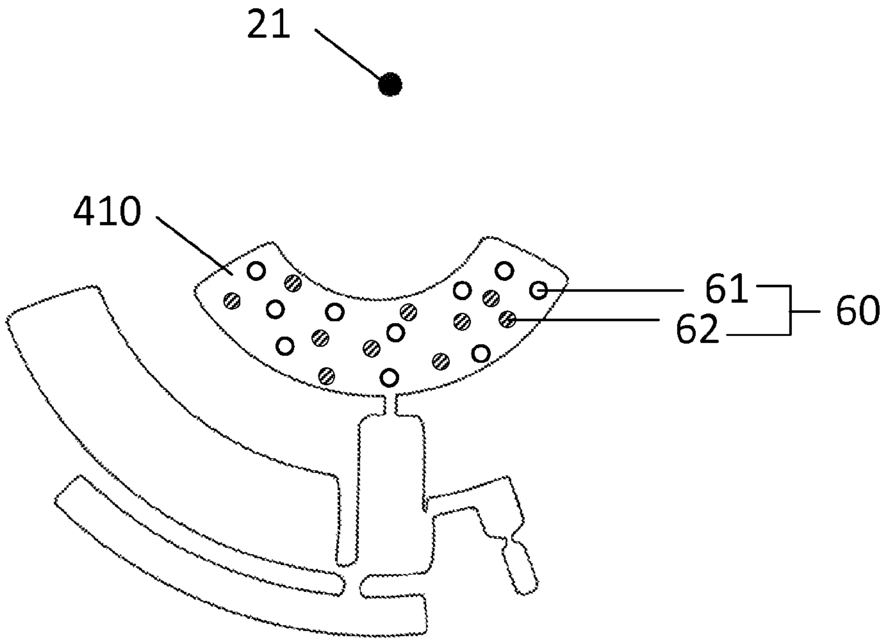

In FIG. 9B, a first test solution 60 is injected into the injection chamber 410 on the microfluidic platform 20 before the gas-based microfluidic device is operated. More particularly, the first test solution 60 comprises low density substances 61 and high density substances 62.

Figure 9C:
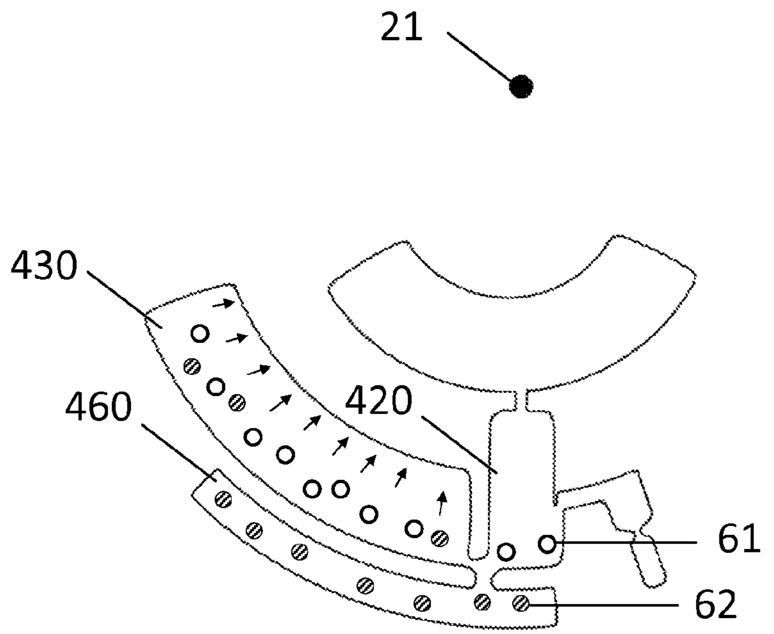

In FIG. 9C, the rotational speed of the drive module 10 is being elevated to a first RPM. Driving by the centrifugal force, the first test solution in the injection chamber 410 is flowing into the process chamber 420 and the storage chamber 460 during the step of increasing the rotational speed. The centrifugal force generated under the first RPM is stronger than the air pressure in the air chamber 430, the first test solution therefore is flowing into the air chamber 430 and compressing the gases in the air chamber 430 until the centrifugal force and the air pressure have reached balance. On the other hand, substances in the first test solution 60 are distributed in the microfluidic element 40A according to the density gradient after drive module 10 has been operating for a period of time. Particularly, the high density substances 62 are mostly stored in the storage chamber 460 which is closer to the exterior side of the microfluidic platform 20, while the low density substances 61 are mostly stored in the process chamber 420 which is closer to the center of rotation 21.

In FIG. 9C, the rotational speed of the drive module 10 is being decreased to a second RPM. The centrifugal force is gradually reduced during the step of decreasing the rotational speed. The compressed gases in the air chamber 430 therefore is decompressing and expelling the first test solution 60 in the air chamber 430.

Figure 9D:
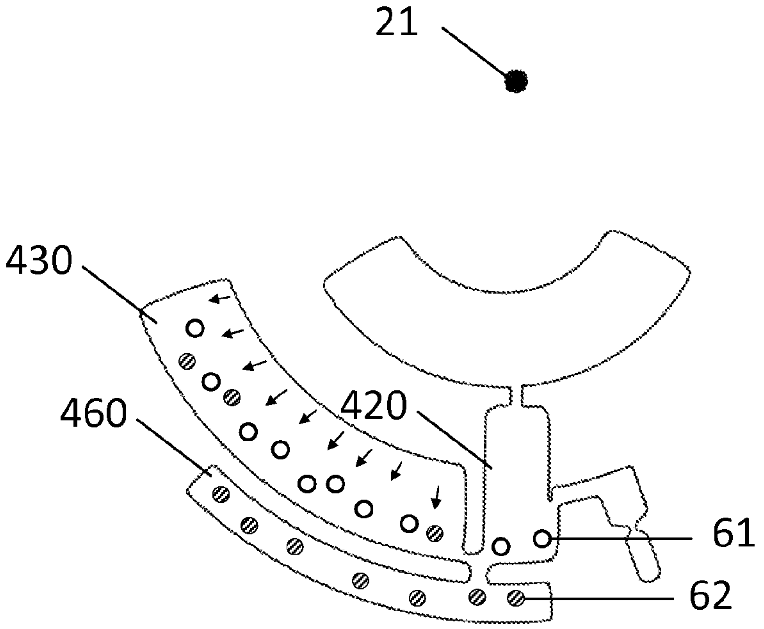
Figure 9E:
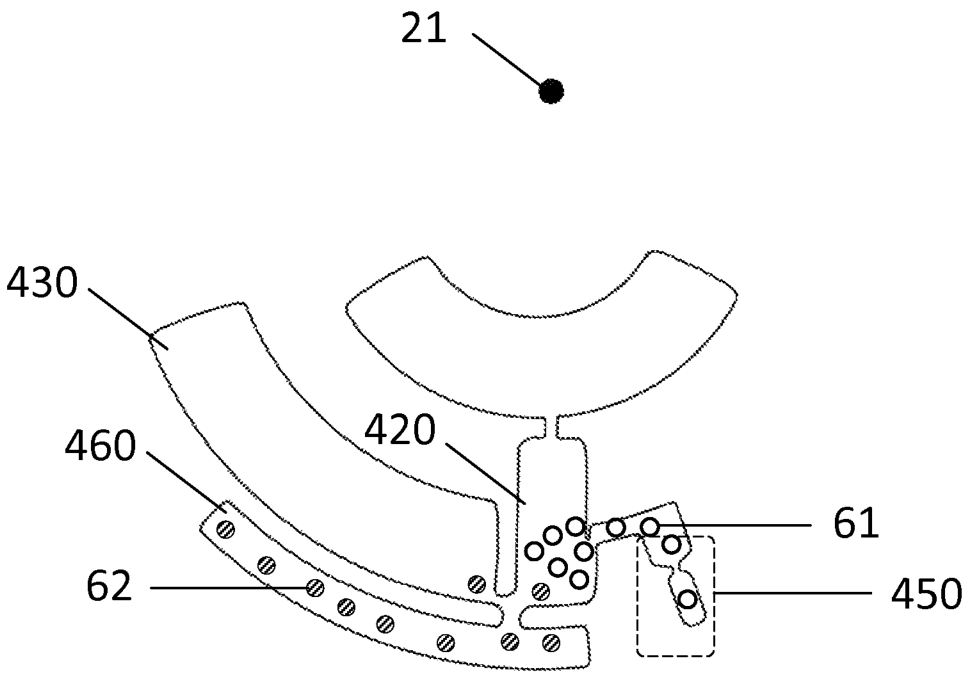

In FIG. 9D, the rotational speed of the drive module 10 has been decreased to the second RPM. The first test solution 60 in the air chamber 430 is actuating by the air pressure and flowing back to the process chamber 420 when the air pressure in the air chamber 430 was stronger than the centrifugal force. The first test solution in the process chamber 420 therefore rose and flowed into the detection chamber 450. More particularly, the high density substances 62 were, as described above, mostly staying in the storage chamber 460 located at the exterior side and the low density substance 61 were mostly in the process chamber 420 and the air chamber 430. Accordingly, most of the first test solution 60 flowed into the detection chamber 450 is the low density substances 61.

Exemplary Use: Milk Quality Testing

One embodiment of the present invention is exemplified by milk quality tests conducted with the gas-based microfluidic device in FIG. 1B, in which the gas-based microfluidic device further comprises the microfluidic element 40B in FIG. 3B and the detection chamber 450A in FIG. 5A. Before performing the testing, 200 μL of milk is injected into the injection chamber 410 on the microfluidic platform 20 and the six reaction chamber 453A are pre-loaded with a glucose test strip, a lactoprotein test strip, a pH test strip, a calcium test strip, a tetracycline test strip, and a chloramphenicol test strip respectively.

During the step that the drive module 10 increases the rotational speed to 5000 RPM, the milk is actuated by the centrifugal force and flows into the process chambers 420, the air chambers 430, and the storage chambers 460. After rotating at 5000 RPM for 100 seconds, the milk had flown into the air chamber 430 and compressed the gases in the air chamber 430. Furthermore, microbes, sediments, and other high density substances in the milk are kept in the storage chamber 460 by the centrifugal force, while lactoproteins and other substances with low sedimentation coefficients remain in the process chamber 420 and the air chamber 430 which are at the exterior side.

During the step that the drive module 10 decreases the rotational speed to 500 RPM, the gases in the air chamber 430 decompress and actuate 80 μL of the milk flowed in the air chamber 430 to move into the overflow channel 440 and the six metering chambers 451A connecting with the overflow channel 440. The six metering chambers 451A herein are identical and each has a capacity of 7 μL. And the milk exceeded the capacity of the six metering chambers 451A will further flow along the overflow channel 440 and move into the waste chamber 470.

After the dispensation process of milk, the drive module 10 increases the rotational speed again to 2000 RPM to elevate the centrifugal force. The milk in the metering chambers 451A will thus overcome the air pressure in the reaction chambers 453A and flow into the reaction chambers 453A. In the last step, the test results on the test strips are read manually or automatically with an image sensor 30.

Exemplary Use: Triglyceride Testing

One embodiment of the present invention is exemplified by triglyceride tests conducted with the gas-based microfluidic device in FIG. 1B. The gas-based microfluidic device further comprises five microfluidic elements 40A in FIG. 3A and one subsidiary microfluidic element 50E in FIG. 6E, in which the subsidiary microfluidic element 50E is connected to the five overflow channels 440 of the five microfluidic elements 40A through give subsidiary intermediate chambers 550E. More particularly, each microfluidic element 40A comprises a detection chamber 450C in FIG. 5C. Furthermore, the microvalve 452C in this embodiment has a burst frequency at 1500 RPM and the subsidiary microvalve 552E has a burst frequency at 2300 RPM.

Before performing the testing, each injection chambers 410 is preloaded with 15 μL blood sample taken from an independent tube from an independent subject, while each subsidiary injection chamber 510E is preloaded with 105 μL triglyceride reagent. The drive module 10 is then activated. During the step that the drive module 10 increases the rotational speed to 4500 RPM, the blood sample in each injection chamber 410 is actuated by the centrifugal force and flows into the process chamber 420, the air chamber 430, and the storage chamber 460. Similarly, the triglyceride reagent in each subsidiary injection chamber 510E flows into the subsidiary process chamber 520E and the subsidiary air chamber 530E.

After rotating at 4500 RPM for 135 seconds, the blood samples and triglyceride reagent had compressed the gases in the air chambers 430 and the subsidiary air chamber 530E respectively. Furthermore, blood cells and other high density substances 62 in the blood sample are deposited in the storage chambers 460 by the centrifugal force, while serum and other low density substances 61 remain in the process chambers 420 and the air chambers 430 which are at the exterior side.

During the step that the drive module 10 decreases the rotational speed to 1200 RPM, the gases in the subsidiary air chamber 530E first decompress and pass the threshold to move the triglyceride regent in the subsidiary air chamber

530E into the subsidiary overflow channel 540E. The triglyceride reagent then follows the subsidiary overflow channel 540E and flows into the five subsidiary metering chambers 551E. Each of the five subsidiary metering chambers 551E herein has a capacity of 15 μL. And the triglyceride reagent exceeded the capacity will further flow along the subsidiary overflow channel 540E and move into the subsidiary waste chamber 570E.

After the dispensing process of triglyceride reagent, the drive module 10 increases the rotational speed again to 2300 RPM. The triglyceride reagent in each subsidiary metering chambers 551E will thus be forced to flow pass the subsidiary microvalves 552E and the microvalves 452C and enter the reaction chambers 453C. The drive module 10 then decreases the rotational speed again to 500 RPM and enables the gases in the air chambers 430 to decompress enough to move the serums to the metering chambers 451C. After the dispensation process of serum, the drive module 10 increases the rotational speed to 1500 RPM to allow the serums to flow pass the microvalves 452C and enter the reaction chambers 453C for reactions. In the last step, the test results are obtained manually or automatically with a detection module 30.

Exemplary Use: Enzymatic Activity Analysis

One embodiment of the present invention is exemplified by enzymatic activity assays conducted with the gas-based microfluidic device in FIG. 1B. The gas-based microfluidic device further comprises a microfluidic element 40C illustrated in FIG. 3C combining with six of the detection chambers 450C in FIG. 5C and six of the subsidiary microfluidic elements 50B in FIG. 6B. The six detection chambers 450C and the six subsidiary microfluidic elements 50B are disposed at the exterior side and the interior side to the overflow channel 430 respectively, in which each detection chamber 450C is paired with a subsidiary microfluidic element 50B. Furthermore, the microvalve 452C in each detection chamber 450C has a burst frequency at 2300 RPM.

Before performing the enzymatic activity assays, 200 μL of blood sample is injected into the injection chamber 410 and 35 μL of buffer solution is injected into each of the six subsidiary injection chambers 510A. On the other hand, the six subsidiary injection chambers 510B are injected with 15 μL of AST substrate, ALT substrate, GPX substrate, amylase substrate, ALP substrate, and GGT substrate respectively.

During the step that the drive module 10 increases the rotational speed to 5000 RPM, the blood sample in the injection chamber 410 is actuated by the centrifugal force and flows into the process chamber 420. Similarly, the substrates in the subsidiary injection chamber 510B flow into the subsidiary process chamber 520B and the buffer solutions in the subsidiary injection chamber 510A flow into the associated reaction chambers 453C respectively under the centrifugal force. After rotating at 5000 RPM for about 85 seconds, the blood samples and the substrates had flown into and compressed the gases in the air chamber 430 and the subsidiary air chamber 530B respectively. Furthermore, blood cells and other high density substances 62 in the blood sample are deposited in the storage chambers 460 by the centrifugal force, while serum and other low density substances 61 remain in the process chambers 420 and the air chambers 430 which are relatively located at the exterior side.

During the step that the drive module 10 decreases the rotational speed to 1200 RPM, the gases in the subsidiary air chambers 530B decompress and pass the threshold to move 5.5 μL of each substrate into the associated metering chamber 451C. The subsequent step increasing the rotational speed to 2300 RPM would then allow the substrates to pass through the microvalve 452C and flow into the reaction chamber 453C for mixing with the buffer solution in the reaction chamber 453C.

After dispensation the substrates, the drive module 10 decreases the rotational speed again to 100 RPM. The gases in the air chamber 430 therefore decompress and pass the threshold to move 50 μL of the serum into the overflow channel 440. Particularly, the six metering chambers 451C are identical and each has a capacity of 6 μL. The excess serum beyond the capacity of the six metering chambers 451C will continue to flow along the overflow channel 440 and enter the waste chamber 470.

After the dispensation process of serum, the drive module 10 increases the rotational speed to 2300 RPM to allow the serum in the metering chambers 451C to flow pass the microvalves 452C and enter each reaction chambers 453C for mixing with the buffer solution and substrate in the reaction chamber 453C respectively. In the last step, the test results of enzymatic activities are obtained manually or automatically with a detection module 30.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A gas-based microfluidic device, comprising:
- a drive module; and
- a microfluidic platform mounted to and rotated by the drive module, comprising:
  - a center of rotation; and
  - at least one microfluidic element, comprising:
    - an injection chamber;
    - a process chamber connected to the injection chamber;
    - an air chamber connected to the process chamber through a first connection channel;
    - an overflow channel connected to the process chamber through a second connection channel, wherein the second connection channel comprises a barrier; and
    - at least one detection chamber connected to the overflow channel.

2. The gas-based microfluidic device as claimed in claim 1, wherein the at least one microfluidic element further comprises:
- a storage chamber connected to the process chamber.

3. The gas-based microfluidic device as claimed in claim 2, wherein the distance between the center of rotation and the first connection channel is greater than that between the center of rotation and the second connection channel.

4. The gas-based microfluidic device as claimed in claim 1, wherein the at least one microfluidic element further comprises:
- a waste chamber connected to the overflow channel.

5. The gas-based microfluidic device as claimed in claim 4, wherein the at least one detection chamber comprises:
- a metering chamber connected to the overflow channel;
- a microvalve connected to the metering chamber; and
- a reaction chamber connected to the microvalve.

6. The gas-based microfluidic device as claimed in claim 1, wherein the at least one microfluidic element further comprises:

at least one air vent connected to the overflow channel.

7. The gas-based microfluidic device as claimed in claim 1, wherein the at least one microfluidic element further comprises:

at least one subsidiary microfluidic element comprising a subsidiary injection chamber connected to the overflow channel.

8. The gas-based microfluidic device as claimed in claim 7, wherein the at least one subsidiary microfluidic element further comprises:

a subsidiary process chamber connected to the subsidiary injection chamber;

a subsidiary air chamber connected to the subsidiary process chamber;

a subsidiary overflow channel connected to the subsidiary process chamber; and at least one subsidiary intermediate chamber connected between the overflow channel and the subsidiary overflow channel.

9. The gas-based microfluidic device as claimed in claim 8, wherein the at least one subsidiary intermediate chamber further comprises:

a subsidiary metering chamber connected to the subsidiary overflow channel;

a subsidiary microvalve connected between the subsidiary metering chamber and the overflow channel.

10. The gas-based microfluidic device as claimed in claim 1, wherein the barrier is a cover-type barrier, a slope-type barrier, or a twin-type barrier.

11. An operating method of gas-based microfluidic devices, comprising:

injecting a first test solution into the injection chamber of the gas-based microfluidic device as claimed in claim 1;

rotating the microfluidic platform to transfer the first test solution in the injection chamber to the process chamber;

increasing the rotational speed to a first RPM to actuate the first test solution to compress a first gas in the air chamber; and decreasing the rotational speed to a second RPM to allow the first gas to actuate the first test solution to flow to the detection chamber.

12. The operating method of gas-based microfluidic devices as claimed in claim 11, wherein in the step of injecting the microfluidic platform, the first test solution comprises high density substances and low density substances.

13. The operating method of gas-based microfluidic devices as claimed in claim 12, wherein in the step of increasing the rotational speed, the high density substances and the low density substances are distributed in the at least one microfluidic element according to the density gradient.

14. The operating method of gas-based microfluidic devices as claimed in claim 12, wherein in the step of decreasing the rotational speed, the first air moves the low density substances to the detection chamber.

15. The operating method of gas-based microfluidic devices as claimed in claim 11, wherein in the step of decreasing the rotational speed, the first air move a predetermined volume of the first test solution to the detection chamber.

16. The operating method of gas-based microfluidic devices as claimed in claim 11, wherein the microfluidic platform further comprises a subsidiary microfluidic element comprising:

a subsidiary overflow channel connected to the detection chamber;

a first subsidiary injection chamber preloaded with a second test solution;

a first subsidiary process chamber connected between the first subsidiary injection chamber and the subsidiary overflow channel;

a first subsidiary air chamber connected to the first subsidiary process chamber, wherein the first subsidiary air chamber contains a second gas;

a second subsidiary injection chamber preloaded with a third test solution;

a second subsidiary process chamber connected between the second subsidiary injection chamber and the subsidiary overflow channel; and a second subsidiary air chamber connected to the second subsidiary process chamber, wherein the second subsidiary air chamber contains a third gas.

17. The operating method of gas-based microfluidic devices as claimed in claim 16, further comprising:

decreasing the rotational speed to a third RPM to allow the second gas to move the second test solution to the detection chamber; and decreasing the rotational speed to a forth RPM to allow the third gas to move the third test solution to the detection chamber.

* * * * *